(12) United States Patent
Iitsuka et al.

(10) Patent No.: US 10,940,463 B2
(45) Date of Patent: Mar. 9, 2021

(54) CATALYST, METHOD FOR PRODUCING CATALYST, AND METHOD FOR PRODUCING ACRYLONITRILE

(71) Applicant: ASAHI KASEI KABUSHIKI KAISHA, Tokyo (JP)

(72) Inventors: Chihiro Iitsuka, Tokyo (JP); Akiyoshi Fukuzawa, Tokyo (JP)

(73) Assignee: ASAHI KASEI KABUSHIKI KAISHA, Tokyo (JP)

(*) Notice: Subject to any disclaimer, the term of this patent is extended or adjusted under 35 U.S.C. 154(b) by 0 days.

(21) Appl. No.: 16/499,832

(22) PCT Filed: Feb. 21, 2019

(86) PCT No.: PCT/JP2019/006650
§ 371 (c)(1),
(2) Date: Sep. 30, 2019

(87) PCT Pub. No.: WO2019/187840
PCT Pub. Date: Oct. 3, 2019

(65) Prior Publication Data
US 2020/0047163 A1 Feb. 13, 2020

(30) Foreign Application Priority Data
Mar. 30, 2018 (JP) .................. 2018-068563

(51) Int. Cl.
| | |
|---|---|
| *B01J 23/88* | (2006.01) |
| *B01J 21/08* | (2006.01) |
| *B01J 37/00* | (2006.01) |
| *B01J 23/887* | (2006.01) |
| *B01J 37/08* | (2006.01) |
| *B01J 37/14* | (2006.01) |
| *B01J 37/16* | (2006.01) |
| *C07C 253/18* | (2006.01) |

(52) U.S. Cl.
CPC ............ *B01J 23/8876* (2013.01); *B01J 21/08* (2013.01); *B01J 37/0072* (2013.01); *B01J 37/08* (2013.01); *B01J 37/14* (2013.01); *B01J 37/16* (2013.01); *C07C 253/18* (2013.01)

(58) Field of Classification Search
None
See application file for complete search history.

(56) References Cited

U.S. PATENT DOCUMENTS

| | | |
|---|---|---|
| 2003/0135064 A1 | 7/2003 | Chaturvedi et al. |
| 2011/0233460 A1 | 9/2011 | Brazdil et al. |
| 2013/0253217 A1 | 9/2013 | Ishii et al. |
| 2017/0352875 A1 | 12/2017 | Miki et al. |
| 2019/0126262 A1 | 5/2019 | Aiki et al. |

FOREIGN PATENT DOCUMENTS

| | | |
|---|---|---|
| JP | 4-12058 A | 1/1992 |
| JP | 2003-181294 A | 7/2003 |
| JP | 2012-245484 A | 12/2012 |
| JP | 2013-527141 A | 6/2013 |
| JP | 2016-120468 A | 7/2016 |
| JP | 2016-213181 A | 12/2016 |
| JP | 2017-199631 A | 11/2017 |
| JP | 2017-220301 A | 12/2017 |
| JP | 2018-44855 A | 3/2018 |
| TW | 201233439 A1 | 8/2012 |
| TW | 201808451 A | 3/2018 |
| WO | WO 2018/047978 A1 | 3/2018 |
| WO | WO 2018/051840 A1 | 3/2018 |

OTHER PUBLICATIONS

International Search Report for PCT/JP2019/006650 (PCT/ISA/210) dated May 21, 2019.
Written Opinion of the International Searching Authority for PCT/JP2019/006650 (PCT/ISA/210) dated May 21, 2019.

*Primary Examiner* — Samantha L Shterengarts
(74) *Attorney, Agent, or Firm* — Birch, Stewart, Kolasch & Birch, LLP

(57) ABSTRACT

The present invention provides a catalyst including Mo, Bi, and Fe, wherein P/R is 0.10 or less, wherein P is a peak intensity at $2\theta=22.9\pm0.2°$ and R is a peak intensity at $2\theta=26.6\pm0.2°$, in X-ray diffraction analysis.

12 Claims, 1 Drawing Sheet

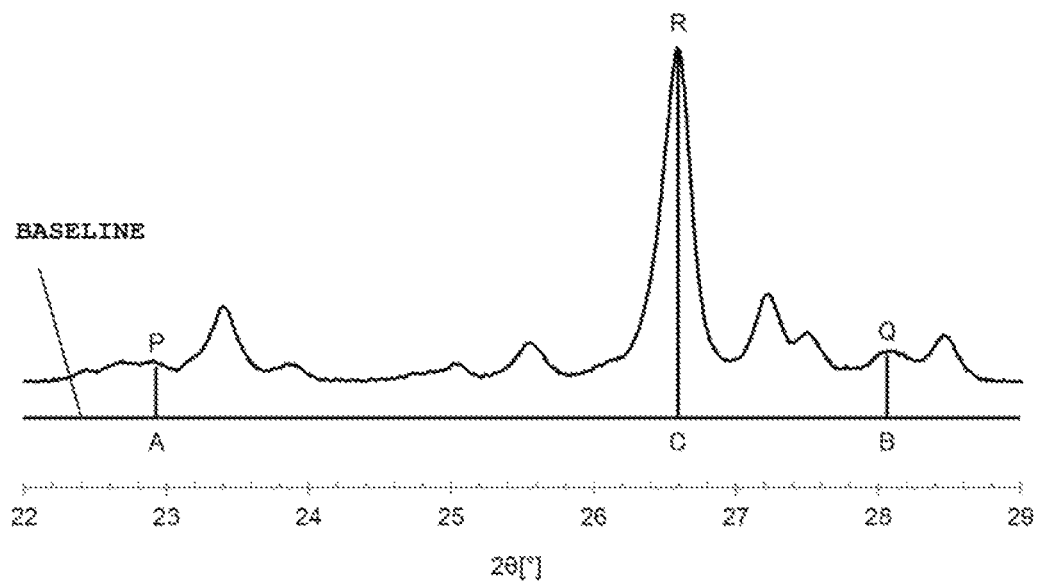

CATALYST, METHOD FOR PRODUCING CATALYST, AND METHOD FOR PRODUCING ACRYLONITRILE

TECHNICAL FIELD

The present invention relates to a catalyst, a method for producing the catalyst, and a method for producing acrylonitrile.

BACKGROUND ART

As a method for producing acrylonitrile, a method in which propylene is subjected to ammoxidation is known. Through this ammoxidation, acrylonitrile and hydrogen cyanide can be obtained at the same time.

As an ammoxidation catalyst, an oxide catalyst comprising molybdenum, bismuth, and iron, or an oxide catalyst comprising antimony and iron are utilized and various improvements have been made to catalysts having these basic compositions, for improving the efficiency of ammoxidation reaction.

For example, it is considered that a catalyst forming a certain peak state in X-ray diffraction analysis described in Patent Literature 1 exhibits high acrylonitrile selectivity and hardly lowers its activity and selectivity in a long-time reaction. In addition, it is considered that a catalyst comprising a certain metal and having a certain peak state in X-ray diffraction analysis described in Patent Literature 2 can suppress production reaction of $CO_2$ and CO produced as side reaction products in the ammoxidation reaction of propylene, isobutene, or tertiary butanol and suppress lowering of selectivity of the object.

CITATION LIST

Patent Literature

[Patent Literature 1] Japanese Unexamined Patent Application Publication No. 2016-120468
[Patent Literature 2] Japanese Unexamined Patent Application Publication No. 2012-245484

SUMMARY OF INVENTION

Technical Problem

In the production of acrylonitrile and hydrogen cyanide, it is generally required to use ammonia in an excessive amount relative to the starting material propylene. Use of ammonia in an excessive amount increases a cost of the production of acrylonitrile and hydrogen cyanide. Therefore, it is an object of the present invention to make ammonia react efficiently and increase the productivity of acrylonitrile and hydrogen cyanide.

The present invention has been completed in consideration of the problems, and an object of the present invention is to efficiently convert ammonia in the ammoxidation reaction for producing acrylonitrile and hydrogen cyanide and increase the productivity of acrylonitrile and hydrogen cyanide.

Solution to Problem

The present inventors have conducted intensive studies to solve the above problems and found that a catalyst comprising at least a certain metallic species and having a peak intensity ratio in X-ray diffraction analysis in a certain range can efficiently convert ammonia in the ammoxidation reaction for producing acrylonitrile and hydrogen cyanide, thereby completed the present invention.

That is, the present invention is as follows.

[1]
A catalyst comprising Mo, Bi, and Fe, wherein:
P/R is 0.10 or less, wherein P is a peak intensity at $2\theta=22.9\pm0.2°$ and R is a peak intensity at $2\theta=26.6\pm0.2°$, in X-ray diffraction analysis.

[2]
The catalyst according to [1], comprising Mo, Bi, and Fe, wherein:
Q/R is 0.06 or more, wherein Q is a peak intensity at $2\theta=28.0\pm0.1°$ and R is a peak intensity at $2\theta=26.6\pm0.2°$, in X-ray diffraction analysis.

[3]
The catalyst according to [1] or [2], wherein the catalyst is represented by formula (1):

$$Mo_{12}Bi_aFe_bX_cY_dZ_eO_f \qquad (1)$$

wherein, X represents at least one element selected from the group consisting of nickel, cobalt, magnesium, calcium, zinc, strontium, barium, and tungsten;
Y represents at least one element selected from the group consisting of cerium, chromium, lanthanum, neodymium, yttrium, praseodymium, samarium, aluminum, boron, gallium, and indium;
Z represents at least one element selected from the group consisting of sodium, potassium, rubidium, and cesium;
a, b, c, d, and e satisfy $0.1 \leq a \leq 2.0$, $0.1 \leq b \leq 4.0$, $0.1 \leq c \leq 10.0$, $0.1 \leq d \leq 3.0$, and $0.01 \leq e \leq 2.0$, respectively; and
f represents a number of oxygen atom needed to satisfy an atomic valence requirement of element existing other than oxygen.

[4]
The catalyst according to [3], wherein a satisfies $0.1 \leq a \leq 0.7$.

[5]
The catalyst according to any one of [1] to [4], wherein the catalyst further comprises silica.

[6]
A method for producing the catalyst according to any one of [1] to [5], comprising:
a step of spray-drying a slurry comprising Mo, Bi, and Fe to obtain a dried particle; and
a step of calcining the dried particle in air and further treating in the presence of a gas that comprises oxygen and ammonia and has 0.1 to 9% by volume of water content.

[7]
A method for producing the catalyst according to any one of [1] to [5], comprising:
a step of spray-drying a slurry comprising Mo, Bi, and Fe to obtain a dried particle; and
a step of calcining the dried particle in air and further treating in the presence of a reducing gas and oxygen.

[8]
The method for producing the catalyst according to [7], wherein an amount of oxygen with respect to the reducing gas (a ratio of oxygen/reducing gas) is 0.3 to 0.95 times a stoichiometric ratio at which the reducing gas is completely combusted.

[9]
A method for producing acrylonitrile comprising a step of reacting propylene, molecular oxygen, and ammonia with each other in the presence of the catalyst according to any one of [1] to [5].

[10]

The method for producing acrylonitrile according to [9], wherein the method is carried out by a fluidized bed reactor.

[11]

The method for producing acrylonitrile according to [9] or [10], wherein a molar ratio of ammonia and air to propylene is in a range of 1.0/(0.8 to 2.5)/(7.0 to 12.0) represented by a ratio of propylene/ammonia/air.

[12]

The method for producing acrylonitrile according to any one of [9] to [11], wherein a reaction is carried out in a temperature range of 300 to 550° C.

Advantageous Effects of Invention

According to the catalyst of the present invention, ammonia can react efficiently in a production method comprising a step of subjecting propylene to ammoxidation and the productivity of acrylonitrile and hydrogen cyanide, which are products obtained by the ammoxidation of propylene, can be improved.

BRIEF DESCRIPTION OF DRAWINGS

FIG. 1 shows a schematic diagram illustrating a spectrum obtained by X-ray diffraction analysis of a catalyst of the present invention.

DESCRIPTION OF EMBODIMENTS

Hereinafter, an embodiment of the present invention (hereinafter, referred to as the "present embodiment") will be described in detail. The present invention is not limited to the following embodiment and can be variously modified within the scope thereof. In the present description, when the numerical value or physical property value is represented by using "to" by describing before and after the "to", values described before and after the "to" are included. For example, the description of a numerical range of "1 to 100" encompasses both its upper limit value "100" and its lower limit value "1". The same applies to the descriptions of other numerical ranges.

[Catalyst]

A catalyst of the present embodiment is a catalyst comprising Mo, Bi, and Fe, wherein P/R is 0.10 or less, wherein P is a peak intensity at $2\theta=22.9\pm0.2°$ and R is a peak intensity at $2\theta=26.6\pm0.2°$, in X-ray diffraction analysis of the catalyst.

By using the catalyst of the present embodiment for ammoxidation of propylene, a reaction substrate, ammonia, can react efficiently.

In the catalyst of the present embodiment, Q/R is preferably 0.03 or more, wherein Q is a peak intensity at $2\theta=28.0\pm0.1°$ and R is a peak intensity at $2\theta=26.6\pm0.2°$ in X-ray diffraction analysis of the catalyst.

The catalyst of the present embodiment exhibits a specific peak in X-ray diffraction analysis.

In X-ray diffraction analysis in the present embodiment, a spectrum schematically shown in FIG. 1 can be obtained by using a CuKα ray as an X-ray source at an anticathode. In this FIGURE, the vertical axis represents diffraction x-ray intensity and the horizontal axis represents 2θ value. The spectrum shown in FIG. 1 is a schematic diagram for describing the peak intensity P, Q, and R in X-ray diffraction analysis of the catalyst of the present embodiment and is not intended to limit the present invention.

As shown in FIG. 1, the peak intensity P at $2\theta=22.9\pm0.2°$ in the present embodiment is a difference of the diffraction x-ray intensity between a point P which is a peak top of $2\theta=22.9\pm0.2°$ on the diffraction pattern and an intersection point A of a perpendicular line dropped from the point P to a baseline, which corresponds to the length of a line segment PA.

In addition, as shown in FIG. 1, the peak intensity Q at $2\theta=28.0\pm0.1°$ is a difference of the diffraction x-ray intensity between a point Q which is a peak top of $2\theta=28.0\pm0.1°$ on the diffraction pattern and an intersection point B of a perpendicular line dropped from the point Q to the baseline, which corresponds to the length of a line segment QB.

Further, as shown in FIG. 1, the peak intensity R at $2\theta=26.6\pm0.2°$ is a difference of the diffraction x-ray intensity between a point R which is a peak top of $2\theta=26.6\pm0.2°$ on the diffraction pattern and an intersection point C of a perpendicular line dropped from the point R to the baseline, which corresponds to the length of a line segment RC.

The peak top in the present description refers to a position exhibiting the maximum value in the spectrum within a given 2θ range. When a plurality of peak tops is present within the given 2θ range, the peak top in the present description is the peak top of a peak which has the highest maximum value.

The baseline is a line connecting, for example, a point having no peak in the vicinity of $2\theta=10°$ to $15°$ and a point having no peak at $2\theta=35°$ to $40°$.

The above "point having no peak" in a XRD measurement refers to, that is, the point on the baseline in a chart in which the vertical axis is defined as diffraction x-ray intensity and the horizontal axis is defined as 2θ, and indicates the point at which no peak is present. Typically, a certain level of diffraction x-ray intensity is exhibited in the portion where no peak is presented (no diffraction point is presented) because a certain level of noise is contained in the XRD measurement. Thus, noise and background are calculated from the calculation of a measuring instrument, that is, from the results of the total analysis and thus, a line at which the diffraction x-ray intensity is almost zero is automatically determined and this line is set as the baseline.

If the baseline is significantly inclined with respect to the X axis representing 2θ, an analysis software attached to the XRD apparatus used in the measurement can be used to appropriately correct a chart so that the baseline can be in parallel with the X axis and respective peak intensities of P, Q, and R can be determined.

P/R in the present embodiment is a ratio of the peak intensity P at $2\theta=22.9\pm0.2°$ to the peak intensity R at $2\theta=26.6\pm0.2°$ and is the value obtained by dividing the peak intensity P by the peak intensity R. P/R is 0.10 or less, preferably 0.09 or less, more preferably 0.08 or less, and further preferably 0.07 or less. The lower limit of P/R is not particularly limited, but it may typically be 0 or more. In addition, the lower limit of P/R may be 0.01 or more, 0.03 or more, or 0.05 or more. By setting P/R to 0.10 or less, the ammonia conversion efficiency and the yield of hydrogen cyanide can be improved.

The range of P/R may be 0 or more and 0.10 or less, 0.01 or more and 0.10 or less, 0.03 or more and 0.10 or less, 0.05 or more and 0.10 or less, or 0.05 or more and 0.09 or less.

Q/R in the present embodiment is a ratio of the peak intensity Q at $2\theta=28.0\pm0.1°$ to the peak intensity R at $2\theta=26.6\pm0.2°$ and is the value obtained by dividing the peak intensity Q by the peak intensity R. Q/R is preferably 0.03 or more, more preferably 0.06 or more, further preferably 0.08 or more, and furthermore preferably 0.10 or more. The upper limit of Q/R is not particularly limited, but it may typically be 0.30 or less. The upper limit of Q/R may be 0.28 or less or 0.25 or less.

The range of Q/R may be 0.03 or more and 0.30 or less, 0.06 or more and 0.30 or less, 0.08 or more and 0.30 or less, 0.10 or more and 0.30 or less, or 0.10 or more and 0.28 or less.

By setting P/R or P/R and Q/R in the above-described range, the ammonia conversion efficiency and the yield of hydrogen cyanide can be improved, and the proportion of acrylonitrile yield in the total yield of acrylonitrile yield and hydrogen cyanide yield can be increased. In addition, by setting Q/R to 0.06 or more, the proportion of acrylonitrile yield in the total yield of acrylonitrile yield and hydrogen cyanide yield can be further increased.

Examples of a method for controlling P/R to 0.10 or less and Q/R to 0.03 or more include a method for adjusting a reduction degree in the catalyst comprising Mo, Bi, and Fe to be higher.

The catalyst of the present embodiment is not particularly limited as long as it comprises at least Mo, Bi, and Fe, and it may comprise other elements.

Examples of the other elements include magnesium and alkali metals.

For example, by comprising magnesium, the crystal phase can be stabilized and there is a tendency that α-transformation of crystal phase, which may lead to a decrease in performance when the catalyst is subjected to fluidized bed reaction, is suppressed. By comprising alkali metal, there is a tendency that production of a by-product is suppressed, and a calcination temperature of the catalyst is held in a preferable range.

The catalyst of the present embodiment is preferably a catalyst represented by formula (1):

$$Mo_{12}Bi_aFe_bX_cY_dZ_eO_f \qquad (1)$$

wherein, X represents at least one element selected from the group consisting of nickel, cobalt, magnesium, calcium, zinc, strontium, barium, and tungsten;

Y represents at least one element selected from the group consisting of cerium, chromium, lanthanum, neodymium, yttrium, praseodymium, samarium, aluminum, boron, gallium, and indium;

Z represents at least one element selected from the group consisting of sodium, potassium, rubidium, and cesium;

a, b, c, d, and e satisfy $0.1 \leq a \leq 2.0$, $0.1 \leq b \leq 4.0$, $0.1 \leq c \leq 10.0$, $0.1 \leq d \leq 3.0$, and $0.01 \leq e \leq 2.0$, respectively; and f represents a number of oxygen atom needed to satisfy an atomic valence requirement of element existing other than oxygen.

The catalyst of the present embodiment may further comprise elements other than those described above.

The atomic ratio a of bismuth to 12 atoms of molybdenum is $0.1 \leq a \leq 2.0$, preferably $0.1 \leq a \leq 0.7$, and more preferably $0.15 \leq a \leq 0.7$.

By setting a to 0.1 or more and 2.0 or less, there is a tendency that yields of producing acrylonitrile and hydrogen cyanide increase and the stability of reaction becomes excellent.

The atomic ratio b of iron to 12 atoms of molybdenum is $0.1 \leq b \leq 4.0$, preferably $0.5 \leq b \leq 3.5$, and more preferably $1.0 \leq b \leq 3.5$.

The atomic ratio c of element X to 12 atoms of molybdenum is $0.1 \leq c \leq 10.0$, preferably $3.0 \leq c \leq 9.0$, and more preferably $4.0 \leq c \leq 8.5$. Element X is at least one selected from the group consisting of nickel, cobalt, magnesium, calcium, zinc, strontium, barium, and tungsten.

The atomic ratio d of element Y to 12 atoms of molybdenum is $0.1 \leq d \leq 3.0$, preferably $0.2 \leq d \leq 2.0$, and more preferably $0.3 \leq d \leq 1.5$. Element Y is at least one selected from the group consisting of cerium, chromium, lanthanum, neodymium, yttrium, praseodymium, samarium, aluminum, boron, gallium, and indium.

The atomic ratio e of element Z to 12 atoms of molybdenum is $0.01 \leq e \leq 2.0$, and preferably $0.05 \leq e \leq 1.5$. Element Z is at least one element selected from the group consisting of sodium, potassium, rubidium, and cesium.

In addition, the atomic ratio f of oxygen to 12 atoms of molybdenum may be a number of oxygen atom needed to satisfy an atomic valence requirement of element existing other than oxygen.

The catalyst of the present embodiment may be made by carrying a metal oxide on a carrier. As the carrier of an ammoxidation catalyst, an oxide such as silica, alumina, titania, or zirconia is used. Silica is preferable from the viewpoint that lowering of the selectivity of the object is small, and the wear resistance and particle strength of the formed particles of the catalyst are good. That is, one of the preferred aspects of the catalyst of the present embodiment is the catalyst further comprising silica.

The amount of a silica carrier used is generally in a range of 20% by mass to 80% by mass, preferably 30% by mass to 70% by mass, and further preferably 40% by mass to 60% by mass based on the total mass of the silica carrier and the metal oxide.

Examples of starting materials of the silica carrier include, but not particularly limited to, silica sol (also referred to as colloidal silica), powdery silica and the like. As the starting material of the silica carrier, silica sol is preferable from the viewpoint of easiness of handling. The average primary particle diameter of silica contained in silica sol is not particularly limited. As the silica carrier, a mixture of different types of silica sol each having a different average primary particle diameter can be used.

[Method for Producing Catalyst]

The catalyst of the present embodiment can be produced by a production method (hereinafter, also referred to as the first production method) comprising: a step of spray-drying a slurry comprising Mo, Bi, and Fe to obtain a dried particle; and a step of calcining the dried particle in air and further treating in the presence of a gas that comprises oxygen and ammonia and has 0.1 to 9% by volume of water content.

In addition, the catalyst of the present embodiment can be produced by a production method (hereinafter, also referred to as the second production method) comprising: a step of spray-drying a slurry comprising Mo, Bi, and Fe to obtain a dried particle; and a step of calcining the dried particle in air and further treating in the presence of a reducing gas and oxygen.

The slurry comprising Mo, Bi, and Fe in the first and the second production methods can be obtained by mixing the starting material of the catalyst and a solvent. The solvent is preferably water, and the slurry is preferably an aqueous slurry. When silica is used for the carrier, a preparation method in which an aqueous solution containing molybdenum is mixed and stirred with an aqueous solution containing silica, and then mixed and stirred with a solution containing bismuth and other metals is preferably used.

In addition, an additive may be added during preparation of solutions of each starting material or the slurry. Examples of the additive include an organic acid.

The starting materials for each element constituting catalysts, such as molybdenum, bismuth, and iron that are used for preparing the slurry, and cerium, nickel, cobalt, magnesium, zinc, potassium, rubidium, and cesium that may be optionally contained may be a salt soluble in water or nitric acid, and examples thereof include ammonium salt, nitrate, hydrochloride, sulfate, organic acid salt of each metal.

The ammonium salt is preferably used as the starting material comprising molybdenum, and the nitrate is preferably used as the starting material comprising bismuth, cerium, iron, nickel, magnesium, zinc, potassium, rubidium, and cesium.

The slurry comprising Mo, Bi, and Fe in the first and the second production methods is spray-dried to prepare the dried particle.

In spray-drying, the slurry is spray-dried to obtain the spherical particle. The spraying of the aqueous slurry is performed by industrially and typically used methods such as a centrifugal method, a two-fluid nozzle method, and a high-pressure nozzle method, and the spraying is preferably performed by the centrifugal method. Heated air is preferably used for drying and examples of a heat source for drying include steam and electric heater. The inlet temperature of the drier is preferably 100° C. to 400° C., and more preferably 150° C. to 300° C. The outlet temperature of the drier is preferably 100° C. to 180° C., and more preferably 110° C. to 170° C.

The dried particle obtained as described above is calcined in air.

The calcination of the dried particle in air is preferably calcined at a temperature in a range of 150° C. to 750° C. and the conditions are not particularly limited, but the calcination is preferably performed by dividing a first step calcination and a second step calcination. In the first step calcination, calcination is preferably performed under the conditions of 150° C. to 450° C. for 30 minutes to 10 hours, and in the second step calcination, calcination is preferably performed under the conditions of 500° C. to 700° C., preferably 520° C. to 650° C., for 1 hours to 20 hours. As an atmosphere gas during the calcination, air is used. For the calcination in air, a calcination furnace such as an electric furnace can be used.

As described above, the catalyst in the present embodiment has P/R of 0.10 or less. Means for obtaining such the catalyst include the method for adjusting the reduction degree in the catalyst comprising Mo, Bi, and Fe to be higher, for example.

Specific examples thereof include a method of supplying the gas that comprises oxygen and ammonia (ammonia gas) and has 0.1 to 9% by volume water content and treating in the presence of the gas subsequent to the calcination (the first production method). As oxygen, air is preferably used. The gas may comprise any gas other than oxygen, ammonia, and water.

The "treating in the presence of the gas that comprises oxygen and ammonia and has 0.1 to 9% by volume of water content" refers to bring the dried particle after calcination into contact with the gas that comprises oxygen and ammonia and has 0.1 to 9% by volume of water content. Specifically, the treatment can be suitably performed by heating the dried particle after calcination in the presence of the gas that comprises oxygen and ammonia and has 0.1 to 9% by volume of water content. The heating temperature is preferably 430° C. to 550° C. In addition, the treatment time is preferably 0.5 hours to 72 hours. The treatment in the presence of the gas that comprises oxygen and ammonia and has 0.1 to 9% by volume of water content can be performed continuously in the calcination furnace used for calcination in air, performed by using a fluidized bed apparatus, or the like, and the treatment is preferably performed by using the fluidized bed apparatus.

The amount of oxygen contained in the gas in the first production method is not particularly limited, and typically 5 to 50% by volume, preferably 10 to 30% by volume, and more preferably 12 to 20% by volume. The amount of ammonia contained in the gas in the first production method is not particularly limited, and typically 5 to 50% by volume, preferably 10 to 30% by volume, and more preferably 12 to 20% by volume.

The volume ratio of ammonia to oxygen in the first production method, that is, ammonia/oxygen is not particularly limited, but is preferably 0.005 to 2.5, more preferably 0.01 to 2.3, and further preferably 0.02 to 2.0.

The water content in the gas to be brought into contacted with the dried particle after calcination is preferably 0.1 to 9% by volume, more preferably 0.15 to 8% by volume, further preferably 0.2 to 7% by volume, and most preferably 0.25 to 6% by volume. By setting the water content to the above-described range, there is a tendency that the efficiency of use of ammonia increases, and yields of acrylonitrile and hydrogen cyanide become excellent, when the ammoxidation reaction is performed by using the catalyst. The influence on the structure of the catalyst (such as P/R) in which the water content in the gas to be brought into contacted with the dried particle after calcination can be obtained is unclear. However, it is presumed that the water content in the above-described range causes reduction of Fe or escape of Mo each contained in the catalyst to progress moderately and thus the crystal structure of the catalyst of the present embodiment is formed.

Other examples of the method for increasing the reduction degree include treating in the presence of the reducing gas and oxygen, subsequent to the calcination (the second production method).

The reducing gas is a gaseous compound exhibiting reducing property and examples thereof include ammonia gas, hydrogen gas, and carbon monoxide gas. These reducing gases may be used singly or in combination of two or more. Ammonia gas is preferable among these reducing gases.

The above-described "treating in the presence of the reducing gas and oxygen" refers to bring the dried particle after calcination into contact with the reducing gas and a molecular oxygen. Air is preferably used as a molecular oxygen source. Specifically, the treatment is preferably performed by heating the dried particle after calcination in the presence of the reducing gas and oxygen. The heating temperature is preferably 350° C. to 500° C. In addition, the treatment time is preferably 0.5 hours to 72 hours.

The treatment in the presence of the reducing gas and oxygen is preferably continuously performed in the calcination furnace that was used for the calcination in air.

The reducing gas and oxygen are supplied to the calcination furnace. The amount of oxygen to the reducing gas supplied is typically 0.3 to 0.95 times, preferably 0.4 to 0.9 times, and more preferably 0.5 to 0.85 times the stoichiometric ratio for complete combustion of the reducing gas. By setting the amount of oxygen with respect to the reducing gas to the above-described range, there is a tendency that the efficiency of use of ammonia is increased, and yields of acrylonitrile and hydrogen cyanide become excellent, when the ammoxidation reaction is performed by using the catalyst.

As the method for increasing the reduction degree, a reducing agent can be added during preparation of the slurry and calcination can be performed in an inert gas atmosphere. The reducing agent refers to a substance that supplies an electron to the other chemical species in an oxidation-reduction reaction. The standard electrode potential can be used as a reference for the strength of the reducing power of the reducing agent. Considering the standard electrode potential of trivalent or bivalent iron, the standard electrode potential of the reducing agent is preferably 0.77 V/SHE (SHE: standard hydrogen electrode) or less. The lower limit of the standard electrode potential of the reducing agent is not particularly limited and for example, −3.0 V/SHE or more. The reducing agent may be added in every stages of the preparation step of the slurry, but all the components constituting the ammoxidation catalyst such as a metal component and a carrier are preferably mixed before the reducing agent is added at the end. In addition, the oxidation-reduction potential of the slurry after addition of the reducing agent is preferably 300 mV/AgCl or less and −300 mV/AgCl or more. The oxidation-reduction potential can be measured by an oxidation-reduction potentiometer (ORP) using a composite electrode (platinum electrode and silver chloride electrode).

The reducing agent is not particularly limited but is preferably the reducing agent that is decomposed under heating in the following spray-drying step or calcination step and that prevents components derived from the reducing agent from remaining in the finally obtained catalyst powder. From the above viewpoints, specific examples of the reducing agent include gallic acid, oxalic acid, formic acid, ascorbic acid, and a hydrazine derivative containing a hydrazine hydrate and/or a hydrazine salt. The hydrazine derivative is preferable among these reducing agents.

The inert gas atmosphere is preferable as the gas atmosphere during the calcination after the spray-drying of the slurry to which the reducing agent was added. Examples of the inert gas include nitrogen. The inert gas is preferably continuously supplied to and exhausted from the calcination system for spreading a gas generated with the decomposition of a metallic salt and the reducing agent in the catalyst powder and the additive, during the calcination in the inert gas atmosphere.

For the calcination in the inert gas atmosphere, the calcination furnace such as the electric furnace can be used.

The shape and particle size of the catalyst of the present embodiment are not particularly limited and when used as a fluidized bed catalyst, the catalyst has preferably a spherical shape and preferably has a particle diameter of 10 to 150 μm, from the viewpoint of fluidity.

[Method for Producing Acrylonitrile and Hydrogen Cyanide]

The method for producing acrylonitrile according to the present embodiment uses the catalyst of the present embodiment. That is, the method for producing acrylonitrile according to the present embodiment comprises a step of reacting propylene, molecular oxygen, and ammonia with each other in the presence of the catalyst of the present embodiment. The production method according to the present embodiment preferably comprises fluidized bed ammoxidation reaction.

By the production method according to the present embodiment, acrylonitrile and hydrogen cyanide can be produced.

The method for producing acrylonitrile according to the present embodiment is preferably performed, for example, in a fluidized bed reactor typically used. Propylene and ammonia each being a starting material are not necessarily of high purity and propylene and ammonia of industrial grade can be used. As the molecular oxygen source, air is typically preferably used and a gas whose oxygen concentration is increased by mixing oxygen with air can be used.

When the molecular oxygen source in the method for producing acrylonitrile according to the present embodiment is air, a composition of a starting material gas (a molar ratio of ammonia and air to propylene) represented by the ratio of propylene/ammonia/air is preferably in the range of 1.0/(0.8 to 2.5)/(7.0 to 12.0), and more preferably in the range of 1/(0.8 to 1.4)/(8 to 11).

The reaction temperature in the method for producing acrylonitrile according to the present embodiment is preferably in the range of 300 to 550° C., and more preferably in the range of 400 to 500° C. The reaction pressure is preferably in the range of normal pressure to 0.3 MPa. The contact time of the starting material gas with the catalyst is preferably 0.5 to 20 (sec·g/cc), and more preferably 1 to 10 (sec·g/cc).

By using the catalyst of the present embodiment, the yield of hydrogen cyanide that is a product of the ammoxidation of propylene can be improved and ammonia can be efficiently converted, in a method for reacting propylene, molecular oxygen, and ammonia with each other. Here, the efficiency of use of ammonia is represented by a ratio of an AN yield to a molar ratio of ammonia/propylene (N/C) when the AN yield is obtained, the "AN yield/N/C". A high AN yield/N/C means increased efficiency of use of ammonia and a low AN yield/N/C means decreased efficiency.

In addition, in the production of acrylonitrile and hydrogen cyanide, the proportion of acrylonitrile that is a main objective product is represented by the "AN proportion". This is the value calculated by the following expression.

AN proportion=100×(acrylonitrile yield/(acrylonitrile yield+hydrogen cyanide yield)

In the above-described production, it is preferable that the yield of hydrogen cyanide be increased without significantly lowering the yield of acrylonitrile that is the main objective product. That is, a high numerical value of AN proportion means a high proportion of acrylonitrile in a product and a low numerical value means a low proportion.

It is preferable that each value of the yield of acrylonitrile and the yield of hydrogen cyanide be high, the value of the above-described N/C be low, and the value of the above-described AN proportion be high.

EXAMPLES

Hereinafter, the present embodiment will be described in more detail giving Examples, but the present embodiment is in no way limited to Examples described below. In addition, evaluation methods of each physical property are as described below.

[X-Ray Diffraction Analysis (XRD Analysis)]

XRD analyses of catalysts obtained in Examples and Comparative Examples are carried out under the following conditions. The catalyst was measured as it is without crushing. If the catalyst is crushed, β-type, divalent metal molybdate crystal phase is transformed to α-type by the impact and no inherent diffraction pattern can be obtained.

Measurement conditions
Detector: semiconductor detector
Tube: Cu
Tube voltage: 40 kV
Tube current: 40 mA
Divergence slit: 0.3°
Step width: 0.02°/step Measurement time: 0.5 sec/step

[Production Condition and Yield of Acrylonitrile and Hydrogen Cyanide by Ammoxidation Reaction of Propylene]

By using the catalyst obtained in Examples and Comparative Examples, acrylonitrile and hydrogen cyanide were produced by ammoxidation reaction of propylene. A Pyrex® glass pipe having an inner diameter of 25 mm and having 16 10-mesh wire nets built-in at an interval of 1 cm was used as a reaction pipe to be used in the ammoxidation reaction.

The reaction was carried out by setting the amount of the catalyst to 50 cc, the reaction temperature to 430° C. and the reaction pressure to 0.17 MPa, and supplying a mixed gas of propylene/ammonia/air at 250 to 450 cc/sec (in terms of NTP) as the total gas flow rate. On that occasion, a propylene content in the mixed gas was set to 9% by volume and a molar ratio of propylene/ammonia/air was set to 1/(0.7 to 1.4)/(8.0 to 13.5). Within this range, an ammonia flow rate was appropriately changed such that the sulfuric acid unit requirement defined by the following expression was 20±2 kg/T-AN, and an air flow rate was appropriately changed such that an oxygen concentration of a gas at an outlet of a reactor was 0.2±0.02% by volume. The molar ratio of ammonia/propylene at this conditions was defined as N/C. In addition, the contact time defined by the following expression was changed by changing the flow rate of the total mixed gas and set such that the conversion rate of propylene defined by the following expression was 99.3±0.2%.

The acrylonitrile yield and the hydrogen cyanide yield produced through the reaction were determined as a value defined by the following expression.

$$\text{Sulfuric acid unit requirement } (kg/T-AN) = \frac{\text{Weight for sulfuric acid needed to neutralize unreacted ammonia (kg)}}{\text{Weight of acrylonitrile produced } (T)}$$

$$\text{Contact time (sec.)} = \frac{\text{Amount of catalyst (cc)}}{\text{Flow rate of mixed gas } (cc-NTP/sec)} \times \frac{2.73}{273 + \text{reaction temperature (°C.)}} \times \frac{\text{Reaction pressure } (MPa)}{0.10}$$

$$\text{Conversion rate of propylene (\%)} = \frac{\text{Propylene consumed (mol)}}{\text{Propylene supplied (mol)}} \times 100$$

$$\text{Acrylonitrile yield (\%)} = \frac{\text{Acrylonitrile produced (mol)}}{\text{Propylene supplied (mol)}} \times 100$$

$$\text{Hydrogen cyanide yield (\%)} = \frac{\text{Hydrogen cyanide produced (mol)}}{\text{Propylene supplied (mol)}} \times 100$$

In addition, AN proportion was calculated from the acrylonitrile yield and the hydrogen cyanide yield according to the following expression.

AN proportion=100×(acrylonitrile yield/(acrylonitrile yield+hydrogen cyanide yield)

An efficiency of use of ammonia uses a value calculated from a ratio of a yield to a molar ratio of ammonia/propylene (N/C) in the case where the AN yield is obtained according to the "AN yield/N/C", as an index.

Example 1

First, a catalyst in which 60% by mass of a metal oxide produced by adjusting the mass of the starting material added such that the composition of the metal oxide was made to be $Mo_{12}Bi_{0.25}Fe_{1.4}Ni_{3.0}Co_{5.8}Ce_{0.40}Rb_{0.12}O_f$ is carried on 40% by mass of silica ($SiO_2$) was produced according to the following procedure.

A mixed liquid of two types of silica was obtained by mixing 666.7 g of aqueous silica sol containing 30% by mass of $SiO_2$ having an average particle diameter of primary particles of 12 nm and 500 g of aqueous silica sol containing 40% by mass of $SiO_2$ having an average particle diameter of primary particles of 41 nm.

Next, a liquid obtained by dissolving 486.2 g of ammonium paramolybdate [$(NH_4)_6Mo_7O_{24}\cdot 4H_2O$] in 870 g of water was added to the mixed liquid of silica sol.

Subsequently, a liquid obtained by dissolving 28.09 g of bismuth nitrate [$Bi(NO_3)_3\cdot 5H_2O$], 131.1 g of iron nitrate [$Fe(NO_3)_3\cdot 9H_2O$], 202.9 g of nickel nitrate [$Ni(NO_3)_2\cdot 6H_2O$], 392.6 g of cobalt nitrate [$Co(NO_3)_2\cdot 6H_2O$], 39.62 g of cerium nitrate [$Ce(NO_3)_3\cdot 6H_2O$], and 4.038 g of rubidium nitrate [$RbNO_3$] in 400 g of a 16.6% by mass concentration nitric acid liquid was added to the mixed liquid to obtain an aqueous raw material mixture (starting material slurry). Next, by using a nebulization apparatus provided with a dish type rotor installed at the center of the upper portion of a drier, spray-drying of the aqueous raw material mixture was performed under conditions of an inlet temperature of about 230° C. and an outlet temperature of about 120° C. Subsequently, preliminary calcination was applied to the dried catalyst precursor at 320° C. for 2 hours in an air atmosphere using an electric furnace, and final calcination was then applied at 600° C. for 2 hours in an air atmosphere. Further, a treatment was applied thereto at 490° C. for 4 hours in the presence of a gas containing 16.3% by volume of oxygen, 17.3% by volume of $NH_3$, and 5.2% by volume water content.

The average particle diameter of the resultant catalyst was 54 μm. The average particle diameter was measured using a laser diffraction/scattering type particle size distribution measurement apparatus LA-300 manufactured by HORIBA, Ltd. It is to be noted that the average particle diameter of the catalysts in Examples and Comparative Examples after this was 52 μm to 55 μm.

XRD analysis was performed on the resultant catalyst according to the method described above to obtain values of P/R and Q/R. The values of P/R and Q/R are shown in Table 1.

In addition, acrylonitrile was produced by ammoxidation reaction of propylene using the resultant catalyst, and acrylonitrile (AN) yield, hydrogen cyanide (HCN) yield, AN proportion, and the ratio of the AN yield to the molar ratio of ammonia/propylene (N/C) (AN yield/N/C) were determined. The results of the AN yield, the HCN yield, the AN proportion, and the AN yield/N/C are shown in Table 1.

In the same manner as in Example 1, the values of P/R and Q/R, the AN yield, the HCN yield, the AN proportion, and the AN yield/N/C were determined in the following Examples and Comparative Examples.

Example 2

The operation was performed in the same manner as in Example 1 except that the treatment was applied at 460° C. for 5 hours in the presence of a gas containing 15.8% by volume of oxygen, 16.8% by volume of $NH_3$, and 8.1% by volume of water content. The measurement results of each property of the resultant catalyst are shown in Table 1.

Example 3

First, a catalyst in which 60% by mass of a metal oxide produced by adjusting the mass of the starting material added such that the composition of the metal oxide was made to be $Mo_{12}Bi_{0.39}Fe_{1.6}Ni_{7.0}Mg_{0.8}Ce_{0.63}Rb_{0.17}O_f$ is carried on 40% by mass of silica ($SiO_2$) was produced according to the following procedure.

To 1333 g of silica sol containing 30% by mass of $SiO_2$ having an average particle diameter of primary particles of 12 nm, 25.0 g of oxalic acid dihydrate dissolved in 200 g of water was added, and 485.9 g of ammonium paramolybdate [$(NH_4)_6Mo_7O_{24}.4H_2O$] dissolved in 873.5 g of water was added under stirring to obtain a mixed liquid containing molybdenum and silica.

Subsequently, a liquid obtained by dissolving 43.1 g of bismuth nitrate [$Bi(NO_3)_3.5H_2O$], 148.0 g of iron nitrate [$Fe(NO_3)_3.9H_2O$], 464.7 g of nickel nitrate [$Ni(NO_3)_2.6H_2O$], 45.5 g of nitric acid magnesium [$Mg(NO_3)_2.6H_2O$], 62.6 g of cerium nitrate [$Ce(NO_3)_3.6H_2O$], and 5.89 g of rubidium nitrate [$RbNO_3$] in 396.7 g of 16.6% by mass nitric acid was added to the above-described mixed liquid to obtain an aqueous raw material mixture (starting material slurry). Next, by using a nebulization apparatus provided with a dish type rotor installed at the center of the upper portion of a drier, spray-drying of the aqueous raw material mixture was performed under conditions of an inlet temperature of about 230° C. and an outlet temperature of about 120° C. Subsequently, preliminary calcination was applied to the dried catalyst precursor using an electric furnace such that the dried catalyst precursor was held at 200° C. for 5 minutes, the temperature was then raised from 200° C. to 450° C. at 2.5° C./min, and the dried catalyst precursor was held at 450° C. for 20 minutes, and thereafter final calcination was applied at 580° C. for 2 hours in an air atmosphere. Further, a treatment was applied at 480° C. for 3 hours in the presence of a gas containing 16.3% by volume of oxygen, 17.4% by volume of $NH_3$, and 4.8% by volume water content. The measurement results of each property of the resultant catalyst are shown in Table 1.

Example 4

First, a catalyst in which 60% by mass of a metal oxide produced by adjusting the mass of the starting material added such that the composition of the metal oxide was made to be $Mo_{12}Bi_{0.30}Fe_{1.7}Ni_{3.5}Co_{4.4}Ce_{0.61}Rb_{0.14}O_f$ is carried on 40% by mass of silica ($SiO_2$) was produced according to the following procedure.

A mixed liquid of two types of silica was obtained by mixing 952.4 g of aqueous silica sol containing 33% by mass of $SiO_2$ having an average particle diameter of primary particles of 12 nm and 198 g of aqueous silica sol containing 40% by mass of $SiO_2$ having an average particle diameter of primary particles of 41 nm. To this mixed liquid of two types of silica, 25.0 g of oxalic acid dihydrate dissolved in 287.5 g of water was added, and 485.6 g of ammonium paramolybdate [$(NH_4)_6Mo_7O_{24}.4H_2O$] dissolved in 866.8 g of water was added under stirring to obtain a mixed liquid containing molybdenum and silica.

Subsequently, a liquid obtained by dissolving 33.8 g of bismuth nitrate [$Bi(NO_3)_3.5H_2O$], 158.2 g of iron nitrate [$Fe(NO_3)_3.9H_2O$], 235.1 g of nickel nitrate [$Ni(NO_3)_2.6H_2O$], 292.2 g of cobalt nitrate [$Co(NO_3)_2.6H_2O$], 60.8 g of cerium nitrate [$Ce(NO_3)_3.6H_2O$], and 4.63 g of rubidium nitrate [$RbNO_3$] in 396 g of 16.6% by mass nitric acid was added to the mixed liquid to obtain an aqueous raw material mixture (starting material slurry). Next, by using a nebulization apparatus provided with a dish type rotor installed at the center of the upper portion of a drier, spray-drying of the aqueous raw material mixture was performed under conditions of an inlet temperature of about 230° C. and an outlet temperature of about 120° C. Subsequently, preliminary calcination was applied to the dried catalyst precursor at 320° C. for 2 hours in an air atmosphere using an electric furnace, and final calcination was then applied at 605° C. for 2 hours in an air atmosphere. Further, a treatment was applied at 465° C. for 9 hours in the presence of a gas containing 16.5% by volume of oxygen, 17.6% by volume of $NH_3$, and 3.9% by volume water content. The measurement results of each property of the resultant catalyst are shown in Table 1.

Example 5

First, a catalyst in which 60% by mass of a metal oxide produced by adjusting the mass of the starting material added such that the composition of the metal oxide was made to be $Mo_{12}Bi_{0.25}Fe_{1.6}Ni_{3.3}Co_{4.1}Ce_{0.58}Rb_{0.12}O_f$ is carried on 40% by mass of silica ($SiO_2$) was produced according to the following procedure.

A mixed liquid of two types of silica was obtained by mixing 952.4 g of aqueous silica sol containing 33% by mass of $SiO_2$ having an average particle diameter of primary particles of 12 nm and 198 g of aqueous silica sol containing 40% by mass of $SiO_2$ having an average particle diameter of primary particles of 41 nm.

Next, a liquid obtained by dissolving 494.886 g of ammonium paramolybdate [$(NH_4)_6Mo_7O_{24}.4H_2O$] in 883 g of water was added to the mixed liquid of silica sol.

Subsequently, a liquid obtained by dissolving 32.61 g of bismuth nitrate [$Bi(NO_3)_3.5H_2O$], 152.6 g of iron nitrate [$Fe(NO_3)_3.9H_2O$], 225.4 g of nickel nitrate [$Ni(NO_3)_2.6H_2O$], 281 g of cobalt nitrate [$Co(NO_3)_2.6H_2O$], 58.62 g of cerium nitrate [$Ce(NO_3)_3.6H_2O$], and 4.145 g of rubidium nitrate [$RbNO_3$] in 395 g of 16.6% by mass concentration nitric acid liquid was added to the mixed liquid to obtain an aqueous raw material mixture (starting material slurry). Next, by using a nebulization apparatus provided with a dish type rotor installed at the center of the upper portion of a drier, spray-drying of the aqueous raw material mixture was performed under conditions of an inlet temperature of about 230° C. and an outlet temperature of about 120° C. Subsequently, preliminary calcination was applied to the dried catalyst precursor at 320° C. for 2 hours in an air atmosphere using an electric furnace, and final calcination was then applied at 590° C. for 2 hours in an air atmosphere. A treatment was applied at 530° C. for 12 hours in the presence of a gas containing 17.0% by volume of oxygen, 18.6% by volume of $NH_3$, and 0.5% by volume water content. The measurement results of each property of the resultant catalyst are shown in Table 1.

Example 6

First, a catalyst in which 60% by mass of a metal oxide produced by adjusting the mass of the starting material added such that the composition of the metal oxide was made to be $Mo_{12}Bi_{0.19}Fe_{2.1}Ni_{3.5}Co_{4.3}Ce_{0.37}Rb_{0.13}O_f$ is carried on 40% by mass of silica ($SiO_2$) was produced according to the following procedure.

A mixed liquid of two types of silica was obtained by mixing 595.2 g of aqueous silica sol containing 33% by mass of $SiO_2$ having an average particle diameter of primary particles of 12 nm and 495.1 g of aqueous silica sol containing 40% by mass of $SiO_2$ having an average particle diameter of primary particles of 41 nm. To this mixed liquid of two types of silica, 25.0 g of oxalic acid dihydrate dissolved in 287.5 g of water was added, and 492.6 g of ammonium paramolybdate $[(NH_4)_6Mo_7O_{24}\cdot4H_2O]$ dissolved in 879.34 g of water was added under stirring to obtain a mixed liquid containing molybdenum and silica.

Subsequently, a liquid obtained by dissolving 21.2 g of bismuth nitrate $[Bi(NO_3)_3\cdot5H_2O]$, 195.0 g of iron nitrate $[Fe(NO_3)_3\cdot9H_2O]$, 237.0 g of nickel nitrate $[Ni(NO_3)_2\cdot6H_2O]$, 295.6 g of cobalt nitrate $[Co(NO_3)_2\cdot6H_2O]$, 37.6 g of cerium nitrate $[Ce(NO_3)_3\cdot6H_2O]$, and 4.36 g of rubidium nitrate $[RbNO_3]$ in 398.9 g of 16.6% by mass nitric acid was added to the mixed liquid to obtain an aqueous raw material mixture (starting material slurry). Next, by using a nebulization apparatus provided with a dish type rotor installed at the center of the upper portion of a drier, spray-drying of the aqueous raw material mixture was performed under conditions of an inlet temperature of about 230° C. and an outlet temperature of about 120° C. Subsequently, preliminary calcination was applied to the dried catalyst precursor at 320° C. for 2 hours in an air atmosphere using an electric furnace, and final calcination was then applied at 605° C. for 2 hours in an air atmosphere. Further, a treatment was applied at 500° C. for 3 hours in the presence of a gas containing 16.5% by volume of oxygen, 17.5% by volume of $NH_3$, and 4.1% by volume water content. The measurement results of each property of the resultant catalyst are shown in Table 1.

Example 7

First, a catalyst in which 60% by mass of a metal oxide produced by adjusting the mass of the starting material added such that the composition of the metal oxide was made to be $Mo_{12}Bi_{0.18}Fe_{2.0}Ni_{3.3}Co_{4.1}Ce_{0.35}Rb_{0.12}O_f$ is carried on 40% by mass of silica ($SiO_2$) was produced according to the following procedure.

To 1190.5 g of aqueous silica sol containing 33% by mass of $SiO_2$ having an average particle diameter of primary particles of 12 nm, 501.6 g of ammonium paramolybdate $[(NH_4)_6Mo_7O_{24}\cdot4H_2O]$ dissolved in 895.4 g of water was added under stirring to obtain a mixed liquid containing molybdenum and silica.

Subsequently, a liquid obtained by dissolving 20.46 g of bismuth nitrate $[Bi(NO_3)_3\cdot5H_2O]$, 187.9 g of iron nitrate $[Fe(NO_3)_3\cdot9H_2O]$, 228.4 g of nickel nitrate $[Ni(NO_3)_2\cdot6H_2O]$, 284.9 g of cobalt nitrate $[Co(NO_3)_2\cdot6H_2O]$, 36.23 g of cerium nitrate $[Ce(NO_3)_3\cdot6H_2O]$, and 4.201 g of rubidium nitrate $[RbNO_3]$ in 398 g of 16.6% by mass concentration nitric acid liquid was added to the mixed liquid to obtain an aqueous raw material mixture (starting material slurry). Next, by using a nebulization apparatus provided with a dish type rotor installed at the center of the upper portion of a drier, spray-drying of the aqueous raw material mixture was performed under conditions of an inlet temperature of about 230° C. and an outlet temperature of about 120° C. Subsequently, preliminary calcination was applied to the dried catalyst precursor at 320° C. for 2 hours in an air atmosphere using an electric furnace, in an air atmosphere, and final calcination was applied at 595° C. for 2 hours. Further, a treatment was applied at 515° C. for 7 hours in the presence of a gas containing 16.6% by volume of oxygen, 18.5% by volume of $NH_3$, and 2.7% by volume water content. The measurement results of each property of the resultant catalyst are shown in Table 1.

Comparative Example 1

The operation was performed in the same manner as in Example 1 except that no treatment was applied to the catalyst in a gas atmosphere in which oxygen, $NH_3$, and water content existed. The measurement results of each property of the resultant catalyst are shown in Table 1.

Comparative Example 2

The operation was performed in the same manner as in Example 1 except that the treatment was applied at 460° C. for 5 hours in the presence of a gas containing 0% by volume of oxygen, 91.9% by volume of $NH_3$, and 8.1% by volume water content. The measurement results of each property of the resultant catalyst are shown in Table 1.

Comparative Example 3

The operation was performed in the same manner as in Example 3 except that the treatment was applied at 480° C. for 3 hours in the presence of a gas containing 15.5% by volume of oxygen, 15.8% by volume of $NH_3$, and 10.3% by volume water content. The measurement results of each property of the resultant catalyst are shown in Table 1.

Comparative Example 4

The operation was performed in the same manner as in Example 4 except that the treatment was applied at 465° C. for 9 hours in the presence of a gas containing 17.2% by volume of oxygen, 17.9% by volume of $NH_3$, and 0% by volume water content. The measurement results of each property of the resultant catalyst are shown in Table 1.

Comparative Example 5

The operation was performed in the same manner as in Example 5 except that the treatment was applied at 530° C. for 12 hours in the presence of a gas containing 20.9% by volume of oxygen, 0% by volume of $NH_3$, and 0.5% by volume water content. The measurement results of each property of the resultant catalyst are shown in Table 1.

Example 8

The treatment was further applied to the catalyst precursor after final calcination obtained in the same manner as in Example 1 at 470° C. for 5 hours in a gas atmosphere in which $NH_3$ is used as a reducing gas and an oxygen/$NH_3$ ratio is 0.6. The measurement results of each property of the resultant catalyst are shown in Table 2.

Example 9

The treatment was further applied to the catalyst precursor after final calcination obtained in the same manner as in Example 3 at 485° C. for 5 hours in a gas atmosphere in which $NH_3$ is used as a reducing gas and an oxygen/$NH_3$ ratio is 0.65. The measurement results of each property of the resultant catalyst are shown in Table 2.

Example 10

The treatment was further applied to the catalyst precursor after final calcination obtained in the same manner as in

Example 11

The treatment was further applied to the catalyst precursor after final calcination obtained in the same manner as in Example 5 at 450° C. for 5 hours in a gas atmosphere in which $NH_3$ is used as a reducing gas and an oxygen/$NH_3$ ratio is 0.7. The measurement results of each property of the resultant catalyst are shown in Table 2.

Example 12

The treatment was further applied to the catalyst precursor after final calcination obtained in the same manner as in Example 6 at 460° C. for 4 hours in a gas atmosphere in which $H_2$ is used as a reducing gas and an oxygen/$H_2$ ratio is 0.4. The measurement results of each property of the resultant catalyst are shown in Table 2.

Example 13

The treatment was further applied to the catalyst precursor after final calcination obtained in the same manner as in Example 7 at 450° C. for 5 hours in a gas atmosphere in which $H_2$ is used as a reducing gas and an oxygen/$H_2$ ratio is 0.36. The measurement results of each property of the resultant catalyst are shown in Table 2.

Comparative Example 6

The operation was performed in the same manner as in Example 9 except that no treatment was applied to the catalyst in a gas atmosphere in which $NH_3$ and oxygen exist. The measurement results of each property of the resultant catalyst are shown in Table 2.

Comparative Example 7

The treatment was further applied to the catalyst precursor after final calcination obtained in the same manner as in Example 4 at 465° C. for 8 hours in an air atmosphere. The measurement results of each property of the resultant catalyst are shown in Table 2.

Comparative Example 8

The treatment was further applied to the catalyst precursor after final calcination obtained in the same manner as in Example 5 at 450° C. for 5 hours in a gas atmosphere in which $NH_3$ is used as a reducing gas and an oxygen/$NH_3$ ratio is 1.2. The measurement results of each property of the resultant catalyst are shown in Table 2.

Example 14

First, a catalyst in which 60% by mass of a metal oxide produced by adjusting the mass of the starting material added such that the composition of the metal oxide is made to be $Mo_{12}Bi_{0.33}Ce_{0.73}Fe_{3.97}Ni_{2.40}Co_{2.99}Rb_{0.08}$ is carried on 40% by mass of silica ($SiO_2$) was produced according to the following procedure.

200.0 g of silica sol containing 30% by mass of $SiO_2$ was held at 40° C. In another container, 72.3 g of ammonium paramolybdate [$(NH_4)_6Mo_7O_{24} \cdot 4H_2O$] was placed and dissolved in 109.1 g of warm water at 60° C. After cooling to 45° C., 5.4 g of 15% by mass ammonia aqueous solution was added to give a molybdenum aqueous solution. Further, after dissolving 10.8 g of cerium nitrate [$Ce(NO_3)_3 \cdot 6H_2O$], 54.8 g of iron nitrate [$Fe(NO_3)_3 \cdot 9H_2O$], 24.0 g of nickel nitrate [$Ni(NO_3)_2 \cdot 6H_2O$], 29.7 g of cobalt nitrate [$Co(NO_3)_2 \cdot 6H_2O$], and 0.38 g of rubidium nitrate [$RbNO_3$] in 60.5 g of water, in another container, the resultant solution was mixed with a solution in which 5.6 g of bismuth nitrate [$Bi(NO_3)_3 \cdot 5H_2O$] and 3.1 g of lactic acid are dissolved in 30 g of water to give a metallic salt aqueous solution. While stirring the silica sol, the molybdenum aqueous solution was added to the silica sol to obtain a silica-molybdenum aqueous solution. Further, while stirring the silica-molybdenum aqueous solution, the metallic salt aqueous solution was added thereto to prepare a slurry. Thereafter, 20.6 g of hydrazine monohydrate (standard electrode potential of hydrazine: −0.33 V/SHE) was added thereto and the slurry was stirred at 60° C. for 90 minutes to prepare a precursor slurry. Next, by using a nebulization apparatus provided with a dish type rotor installed at the center of the upper portion of a drier, spray-drying of the aqueous raw material mixture was performed under conditions of an inlet temperature of about 230° C. and an outlet temperature of about 120° C. Subsequently, the dried catalyst precursor was held at 90° C. for 15 hours under vacuum. Further, in the catalyst precursor after held under vacuum, the temperature was raised from 30° C. to 640° C. for 9 hours in a nitrogen atmosphere and the catalyst precursor was calcined at 640° C. for 3 hours and 30 minutes to obtain a catalyst.

P/R and Q/R of the resultant catalyst were 0.09 and 0.05, respectively. In addition, the AN yield was 83.2%, the HCN yield was 3.5%, the AN proportion was 96.2%, N/C was 1.19, and the AN yield/N/C was 70.

TABLE 1

| | Catalyst composition | | | | | | | | Treatment conditions with gas containing oxygen, $NH_3$, and water | |
|---|---|---|---|---|---|---|---|---|---|---|
| | | | | | | | | | Oxygen | $NH_3$ |
| | Mo | Bi | Fe | Ni | Co | Ce | Mg | Rb | Silica [wt. %] | [% by volume] | [% by volume] |
| Example 1 | 12 | 0.25 | 1.4 | 3.0 | 5.8 | 0.40 | — | 0.12 | 40 | 16.3 | 17.3 |
| Example 2 | 12 | 0.25 | 1.4 | 3.0 | 5.8 | 0.40 | — | 0.12 | 40 | 15.8 | 16.8 |
| Example 3 | 12 | 0.39 | 1.6 | 7.0 | — | 0.63 | 0.8 | 0.17 | 40 | 16.3 | 17.4 |
| Example 4 | 12 | 0.30 | 1.7 | 3.5 | 4.4 | 0.61 | — | 0.14 | 40 | 16.5 | 17.6 |
| Example 5 | 12 | 0.29 | 1.6 | 3.3 | 4.1 | 0.58 | — | 0.12 | 40 | 17.0 | 18.6 |
| Example 6 | 12 | 0.19 | 2.1 | 3.5 | 4.3 | 0.37 | — | 0.13 | 40 | 16.5 | 17.5 |
| Example 7 | 12 | 0.18 | 2.0 | 3.3 | 4.1 | 0.35 | — | 0.12 | 40 | 16.6 | 18.5 |

TABLE 1-continued

|  | Mo | Bi | Fe | Ni | Co | Ce | Mg | Rb | Silica [wt. %] | | |
|---|---|---|---|---|---|---|---|---|---|---|---|
| Comparative Example 1 | 12 | 0.25 | 1.4 | 3.0 | 5.8 | 0.40 | — | 0.12 | 40 | — | — |
| Comparative Example 2 | 12 | 0.25 | 1.4 | 3.0 | 5.8 | 0.40 | — | 0.12 | 40 | 0 | 91.9 |
| Comparative Example 3 | 12 | 0.39 | 1.6 | 7.0 | — | 0.63 | 0.8 | 0.17 | 40 | 15.5 | 15.8 |
| Comparative Example 4 | 12 | 0.30 | 1.7 | 3.5 | 4.4 | 0.61 | — | 0.14 | 40 | 17.2 | 17.9 |
| Comparative Example 5 | 12 | 0.29 | 1.6 | 3.3 | 4.1 | 0.58 | — | 0.12 | 40 | 20.9 | 0 |

| | Treatment conditions with gas containing oxygen, NH$_3$, and water | | | Reaction evaluation results | | | | | |
|---|---|---|---|---|---|---|---|---|---|
| | Water [% by volume] | Temperature [° C.] | Time [h] | X-ray diffraction | | AN yield [%] | HCN yield [%] | AN proportion [%] | AN yield/ |
| | | | | P/R | Q/R | | | | N/C | N/C |
| Example 1 | 5.2 | 490 | 4 | 0.08 | 0.21 | 83.8 | 3.2 | 96.3 | 1.12 | 75 |
| Example 2 | 8.1 | 460 | 5 | 0.06 | 0.22 | 83.6 | 3.4 | 96.1 | 1.11 | 75 |
| Example 3 | 4.8 | 480 | 3 | 0.07 | 0.10 | 83.7 | 3.3 | 96.2 | 1.12 | 75 |
| Example 4 | 3.9 | 465 | 9 | 0.08 | 0.07 | 83.6 | 3.4 | 96.1 | 1.20 | 70 |
| Example 5 | 0.5 | 530 | 12 | 0.09 | 0.03 | 83.7 | 3.8 | 95.7 | 1.19 | 70 |
| Example 6 | 4.1 | 500 | 3 | 0.08 | 0.08 | 83.4 | 3.7 | 95.8 | 1.19 | 70 |
| Example 7 | 2.7 | 515 | 7 | 0.07 | 0.04 | 82.6 | 3.9 | 95.5 | 1.14 | 72 |
| Comparative Example 1 | — | — | — | 0.18 | 0.08 | 84.2 | 3.0 | 96.6 | 1.23 | 68 |
| Comparative Example 2 | 8.1 | 460 | 5 | 0.14 | 0.05 | 78.1 | 3.7 | 95.5 | 1.18 | 66 |
| Comparative Example 3 | 10.3 | 480 | 3 | 0.11 | 0.04 | 81.9 | 3.2 | 96.2 | 1.18 | 69 |
| Comparative Example 4 | 0 | 465 | 9 | 0.11 | 0.06 | 83.3 | 3.2 | 96.3 | 1.22 | 68 |
| Comparative Example 5 | 0.5 | 530 | 12 | 0.12 | 0.03 | 83.9 | 3.1 | 96.4 | 1.31 | 64 |

TABLE 2

| | Catalyst composition | | | | | | | | | Treatment conditions with reducing gas | |
|---|---|---|---|---|---|---|---|---|---|---|---|
| | Mo | Bi | Fe | Ni | Co | Ce | Mg | Rb | Silica [wt. %] | Reducing gas type | Oxygen/ reducing gas ratio |
| Example 8 | 12 | 0.25 | 1.4 | 3.0 | 5.8 | 0.40 | — | 0.12 | 40 | NH$_3$ | 0.6 |
| Example 9 | 12 | 0.39 | 1.6 | 7.0 | 0.0 | 0.63 | 0.8 | 0.17 | 40 | NH$_3$ | 0.65 |
| Example 10 | 12 | 0.30 | 1.7 | 3.5 | 4.4 | 0.61 | — | 0.14 | 40 | NH$_3$ | 0.7 |
| Example 11 | 12 | 0.29 | 1.6 | 3.3 | 4.1 | 0.58 | — | 0.12 | 40 | NH$_3$ | 0.7 |
| Example 12 | 12 | 0.19 | 2.1 | 3.5 | 4.3 | 0.37 | — | 0.13 | 40 | H$_2$ | 0.4 |
| Example 13 | 12 | 0.18 | 2.0 | 3.3 | 4.1 | 0.35 | — | 0.12 | 40 | H$_2$ | 0.36 |
| Comparative Example 6 | 12 | 0.39 | 1.6 | 7.0 | — | 0.63 | 0.8 | 0.17 | 40 | — | — |
| Comparative Example 7 | 12 | 0.30 | 1.7 | 3.5 | 4.4 | 0.61 | — | 0.14 | 40 | — | — |
| Comparative Example 8 | 12 | 0.29 | 1.6 | 3.3 | 4.1 | 0.58 | — | 0.12 | 40 | NH$_3$ | 1.2 |

| | Treatment conditions with reducing gas | | Reaction evaluation results | | | | | | |
|---|---|---|---|---|---|---|---|---|---|
| | Temperature [° C.] | Time [h] | X-ray diffraction | | AN yield [%] | HCN yield [%] | AN proportion [%] | | AN yield/ |
| | | | P/R | Q/R | | | | N/C | N/C |
| Example 8 | 470 | 5 | 0.06 | 0.22 | 83.8 | 3.4 | 96.1 | 1.13 | 74 |
| Example 9 | 485 | 5 | 0.06 | 0.12 | 83.7 | 3.5 | 96.0 | 1.12 | 75 |
| Example 10 | 465 | 8 | 0.07 | 0.07 | 83.6 | 3.6 | 95.9 | 1.20 | 70 |
| Example 11 | 450 | 5 | 0.06 | 0.05 | 83.6 | 3.9 | 95.5 | 1.19 | 70 |
| Example 12 | 460 | 4 | 0.07 | 0.04 | 83.3 | 3.9 | 95.5 | 1.18 | 71 |
| Example 13 | 450 | 5 | 0.06 | 0.03 | 82.6 | 4.1 | 95.3 | 1.14 | 72 |

TABLE 2-continued

| | | | | | | | | | |
|---|---|---|---|---|---|---|---|---|---|
| Comparative Example 6 | — | — | 0.13 | 0.05 | 84 | 3.2 | 96.3 | 1.21 | 69 |
| Comparative Example 7 | 465 | 8 | 0.12 | 0.05 | 84.1 | 3.0 | 96.5 | 1.23 | 68 |
| Comparative Example 8 | 450 | 5 | 0.14 | 0.04 | 84.1 | 2.9 | 96.7 | 1.31 | 64 |

The present application is based on the Japanese Patent Application (Japanese Patent Application No. 2018-068563) filed on 30 Mar. 2018, the contents of which are incorporated herein by reference.

INDUSTRIAL APPLICABILITY

The catalyst of the present invention has industrial applicability in the production of acrylonitrile and hydrogen cyanide including a step of subjecting propylene to ammoxidation.

The invention claimed is:

1. A catalyst comprising Mo, Bi, and Fe, wherein:
P/R is 0.10 or less, wherein P is a peak intensity at 2θ=22.9±0.2° and R is a peak intensity at 2θ=26.6±0.2°, in X-ray diffraction analysis.

2. The catalyst according to claim 1, comprising Mo, Bi, and Fe, wherein:
Q/R is 0.06 or more, wherein Q is a peak intensity at 2θ=28.0±0.1° and R is a peak intensity at 2θ=26.6±0.2°, in X-ray diffraction analysis.

3. The catalyst according to claim 1, wherein the catalyst is represented by formula (1):

$$Mo_{12}Bi_aFe_bX_cY_dZ_eO_f \qquad (1)$$

wherein, X represents at least one element selected from the group consisting of nickel, cobalt, magnesium, calcium, zinc, strontium, barium, and tungsten;
Y represents at least one element selected from the group consisting of cerium, chromium, lanthanum, neodymium, yttrium, praseodymium, samarium, aluminum, boron, gallium, and indium;
Z represents at least one element selected from the group consisting of sodium, potassium, rubidium, and cesium;
a, b, c, d, and e satisfy $0.1 \leq a \leq 2.0$, $0.1 \leq b \leq 4.0$, $0.1 \leq c \leq 10.0$, $0.1 \leq d \leq 3.0$, and $0.01 \leq e \leq 2.0$, respectively; and
f represents a number of oxygen atom needed to satisfy an atomic valence requirement of element existing other than oxygen.

4. The catalyst according to claim 3, wherein a satisfies $0.1 \leq a \leq 0.7$.

5. The catalyst according to claim 1, wherein the catalyst further comprises silica.

6. A method for producing the catalyst according to claim 1, comprising:
a step of spray-drying a slurry comprising Mo, Bi, and Fe to obtain a dried particle; and
a step of calcining the dried particle in air and further treating in the presence of a gas that comprises oxygen and ammonia and has 0.1 to 9% by volume of water content.

7. A method for producing the catalyst according to claim 1, comprising:
a step of spray-drying a slurry comprising Mo, Bi, and Fe to obtain a dried particle; and
a step of calcining the dried particle in air and further treating in the presence of a reducing gas and oxygen.

8. The method for producing the catalyst according to claim 7, wherein an amount of oxygen with respect to the reducing gas (a ratio of oxygen/reducing gas) is 0.3 to 0.95 times a stoichiometric ratio at which the reducing gas is completely combusted.

9. A method for producing acrylonitrile comprising a step of reacting propylene, molecular oxygen, and ammonia with each other in the presence of the catalyst according to claim 1.

10. The method for producing acrylonitrile according to claim 9, wherein the method is carried out by a fluidized bed reactor.

11. The method for producing acrylonitrile according to claim 9, wherein a molar ratio of ammonia and air to propylene is in a range of 1.0/(0.8 to 2.5)/(7.0 to 12.0) represented by a ratio of propylene/ammonia/air.

12. The method for producing acrylonitrile according to claim 9, wherein a reaction is carried out in a temperature range of 300 to 550° C.

* * * * *